(12) United States Patent
Mei et al.

(10) Patent No.: US 10,371,551 B2
(45) Date of Patent: Aug. 6, 2019

(54) SYSTEM AND METHOD FOR CALCULATING FLOW VELOCITY

(71) Applicant: General Electric Company, Schenectady, NY (US)

(72) Inventors: Yan Mei, Shanghai (CN); Ran Nui, Shanghai (CN); Weihua Shang, Shanghai (CN); Gang Cheng, Shanghai (CN); Jing Ye, Shanghai (CN); Longtao Yuan, Shanghai (CN)

(73) Assignee: General Electric Company, Schenectady, NY (US)

( * ) Notice: Subject to any disclaimer, the term of this patent is extended or adjusted under 35 U.S.C. 154(b) by 35 days.

(21) Appl. No.: 15/533,665

(22) PCT Filed: Dec. 10, 2015

(86) PCT No.: PCT/US2015/064967
§ 371 (c)(1),
(2) Date: Jun. 7, 2017

(87) PCT Pub. No.: WO2016/094643
PCT Pub. Date: Jun. 16, 2016

(65) Prior Publication Data
US 2017/0343399 A1 Nov. 30, 2017

(30) Foreign Application Priority Data

Dec. 10, 2014 (CN) .......................... 2014 1 0756540

(51) Int. Cl.
*G01F 1/66* (2006.01)
*G01N 29/024* (2006.01)

(52) U.S. Cl.
CPC .............. *G01F 1/663* (2013.01); *G01F 1/667* (2013.01); *G01N 29/024* (2013.01); *G01N 2291/02836* (2013.01)

(58) Field of Classification Search
CPC ........................................................ G01F 1/66
See application file for complete search history.

(56) References Cited

U.S. PATENT DOCUMENTS

| 5,148,229 A | 9/1992 | Wiseall |
| 5,521,883 A | 5/1996 | Fage et al. |
(Continued)

FOREIGN PATENT DOCUMENTS

| CN | 101802562 A | 8/2010 |
| CN | 102174887 A | 9/2011 |
(Continued)

OTHER PUBLICATIONS

Johnson, S.A., et al., "Reconstructing Three-Dimensional Fluid Velocity Vector Fields From Acoustic Transmission Measurements," Acoustical Holography, vol. 7, pp. 307-326 (1977).
Pihl, M.J., et al., "Measuring 3D velocity vectors using the Transverse Oscillation method," IEEE International Ultrasonics Symposium (IUS), pp. 1881-1885 (2012).
(Continued)

*Primary Examiner* — Jewel V Dowtin
(74) *Attorney, Agent, or Firm* — Laura L. Pollander

(57) ABSTRACT

A system and method for calculation of flow rate comprising at least two ultrasonic sensors, ultrasonic transmit receive device, and signal processing device. At least two ultrasonic sensors are installed on the pipe where the fluid is flowing through, and at least two ultrasonic sensors contain different ultrasonic beam paths, further, the ultrasonic beam paths of at least two ultrasonic sensors contain the overlap area. The ultrasonic transmit and receive device is used to actuate at least two ultrasonic sensors, and is used to transmit one or multiple ultrasonic signals to pipes via one or multiple of at least two ultrasonic sensors, further, to receive ultrasonic signal via at least two ultrasonic sensors. The signal processing device is used to process the ultrasonic signal received, further, to calculate the flow rate of the fluid precisely.

20 Claims, 6 Drawing Sheets

(56) References Cited

U.S. PATENT DOCUMENTS

| | | | |
|---|---|---|---|
| 6,067,861 A | 5/2000 | Shekarriz et al. | |
| 6,243,657 B1 | 6/2001 | Tuck et al. | |
| 7,044,001 B2* | 5/2006 | Sylvia | G01F 1/662 |
| | | | 73/861.29 |
| 7,096,719 B2 | 8/2006 | Gysling | |
| 7,389,187 B2 | 6/2008 | Kersey et al. | |
| 7,581,453 B2 | 9/2009 | Ao et al. | |
| 8,562,531 B2 | 10/2013 | Yoshikawa et al. | |
| 9,453,749 B1* | 9/2016 | Bachmann | G01F 15/00 |
| 9,945,737 B2* | 4/2018 | DeSilva | G01K 1/20 |
| 10,036,763 B2* | 7/2018 | Hies | G01P 5/244 |
| 10,088,348 B2* | 10/2018 | Xu | G01F 1/66 |
| 2008/0156107 A1* | 7/2008 | Ao | G01F 1/663 |
| | | | 73/861.27 |
| 2010/0294045 A1 | 11/2010 | Laurent | |
| 2011/0098938 A1 | 4/2011 | Huang et al. | |
| 2011/0271769 A1 | 11/2011 | Kippersund et al. | |
| 2013/0345994 A1 | 12/2013 | Wiklund et al. | |
| 2016/0305805 A1* | 10/2016 | Baumoel | G01F 1/663 |
| 2017/0167904 A1* | 6/2017 | Sathyanarayana | G01F 1/662 |
| 2018/0149505 A1* | 5/2018 | Ploss | G01F 1/667 |

FOREIGN PATENT DOCUMENTS

| | | |
|---|---|---|
| CN | 102288780 A | 12/2011 |
| CN | 103926422 A | 7/2014 |
| CN | 104007287 A | 8/2014 |
| CN | 104121955 A | 10/2014 |
| WO | 2004/032745 A2 | 4/2004 |

OTHER PUBLICATIONS

International Search Report and Written Opinion issued in connection with corresponding PCT Application No. PCT/US2015/064967 dated Mar. 22, 2016.

International Preliminary Report on Patentability issued in connection with corresponding PCT Application No. PCT/US2015/064967 dated Jun. 13, 2017.

Machine Translation and First Office Action and Search issued in connection with corresponding CN Application No. 201410756540.2 dated Jun. 4, 2018.

Office Action issued in connection with corresponding MX Application No. MX/A/2017/007589 dated Oct. 4, 2018.

* cited by examiner

SYSTEM AND METHOD FOR CALCULATING FLOW VELOCITY

TECHNICAL FIELD

Embodiments involve a system and method for calculating flow rate, particularly a system and method used for calculating flow rate during drilling process.

BACKGROUND

During drilling process, the swiveling drilling bit is installed on the drill rod, the sea level platform conducts the control to drill bit via the drill rod, and the drill rod drives the drill bit swiveling, in which way, the shaft is drilled out under seabed. During the mentioned period, the drilling fluid in the fluid tank that installed on the sea level platform reaches the drill bit via drill rod, then return to the fluid tank via the annular space formed between the drill rod and riser pipe. The drilling fluid maintains a certain level of hydrostatic pressure to balance the pressure of fluid from shaft and to cool down the drill bit. In addition, the drilling fluid mixes with the material generated during the formation of shaft to return and carry back the material to the sea surface for treatment.

During drilling process, when the pressure of fluid entering the shaft from the wellbore is larger than the pressure of drilling fluid, the fluid in strata enters the annular space with the drilling fluid, in this way, it would be generated that the drilling fluid is returned with greater pressure, further, there is a blowout in case of loss of control. Therefore, monitoring and measuring the returned drilling fluid in real time is necessary to determine whether the blowout will occur. In general, the flow rate of drilling fluid returned is measured to determine whether the fluid changes to monitor the occurrence of blowout, and to ensure the safety operation of drilling.

Drawing 1A shows the axial schematic drawing of a riser pipe and drawing 1B shows the horizontal schematic drawing of a riser pipe. As shown in drawing 1A and 1B, it is known that the flow rate $v_i$ of the drilling fluid 130 returned (as shown in drawing 3) that flowing in the riser pipe 11 in the direction in parallel with ultrasonic beam path could be calculated, then, under the condition that without any consideration of the horizontal flow rate component $v_R$ of the drilling fluid 130 returned, the flow rate $v_i$ of the drilling fluid 130 returned in the direction that in parallel with the ultrasonic beam path is directly projected on to the axial direction (i.e. z axle direction), to calculate the axial flow rate $v_z$ of the drilling fluid 130 returned, i.e. the flow rate component $v_z$ in z axle direction. However, in actual operation, the drill bit would move frequently, further, when the drill bit moves, it would be obvious that the contribution of the horizontal flow rate component $v_R$ of the drilling fluid 130 returned, at this time, it cannot be ignored that the horizontal flow rate component $v_R$ of the drilling fluid 130 returned. Under this condition, that the axial flow rate $v_z$ and the horizontal flow rate component $v_R$ of the drilling fluid 130 returned by utilizing one ultrasonic sensor could not be calculated, i.e. the two-dimensional flow rate of the drilling fluid 130 returned. Further, the horizontal flow rate component $v_R$ could be divided as the flow rate component $v_x$ in the x-axle direction and $v_y$ in y-axle direction. Therefore, the flow rate components $v_x$, $v_y$ and $v_z$ of the drilling fluid 130 returned in the x-axle, y-axle and z-axle direction could not be calculated by utilizing one ultrasonic sensor, i.e. the three-dimensional flow rate of the drilling fluid 130 returned.

Therefore, it is necessary to provide an improved system and method to solve at least one of the above-mentioned problems.

SUMMARY

Embodiments provide a system that is used to calculate the flow rate on one hand, which contains at least two ultrasonic sensors, ultrasonic transmit and receive device and signal processing device. Wherein, the mentioned two ultrasonic sensors are installed on the pipe where the fluid is flowing through, the mentioned at least two ultrasonic sensors contain different ultrasonic beam paths, further, the ultrasonic beam paths of the mentioned at least two ultrasonic sensors contain the overlap area. The ultrasonic transmit and receive device is used to actuate the mentioned at least two ultrasonic sensors, and is used to transmit one or multiple ultrasonic signals to the mentioned pipe via one or multiple of the mentioned at least two ultrasonic sensors, further, to receive the ultrasonic signal via the mentioned at least two ultrasonic sensors. The signal processing device is used to process the mentioned ultrasonic signal received, and to calculate the flow rate of the mentioned fluid.

Additionally, an embodiment provides a method for calculating the flow rate, which contains that: transmitting one or multiple ultrasonic signal to the pipe via one or multiple of at least two ultrasonic sensors, the ultrasonic beam paths of the mentioned at least two ultrasonic sensors crossing with each other with overlap area; receiving the ultrasonic signal via the mentioned at least two ultrasonic sensors; processing the mentioned ultrasonic signal received, to calculate the flow rate of fluid which is flowing through the mentioned pipe.

The system and method that is used to calculate the flow rate of embodiments of this invention could be applied on multiple domains, with high application value and reliability in the field.

BRIEF DESCRIPTION OF THE DRAWINGS

When reading the following detailed description with reference to the attached drawings, these and other technical characters, aspects and advantages of this invention would become more comprehensible, further, within attached drawings, the same component marks in the entire attached drawings would be used to represent the same component, wherein.

DETAILED DESCRIPTION

Figure 1:
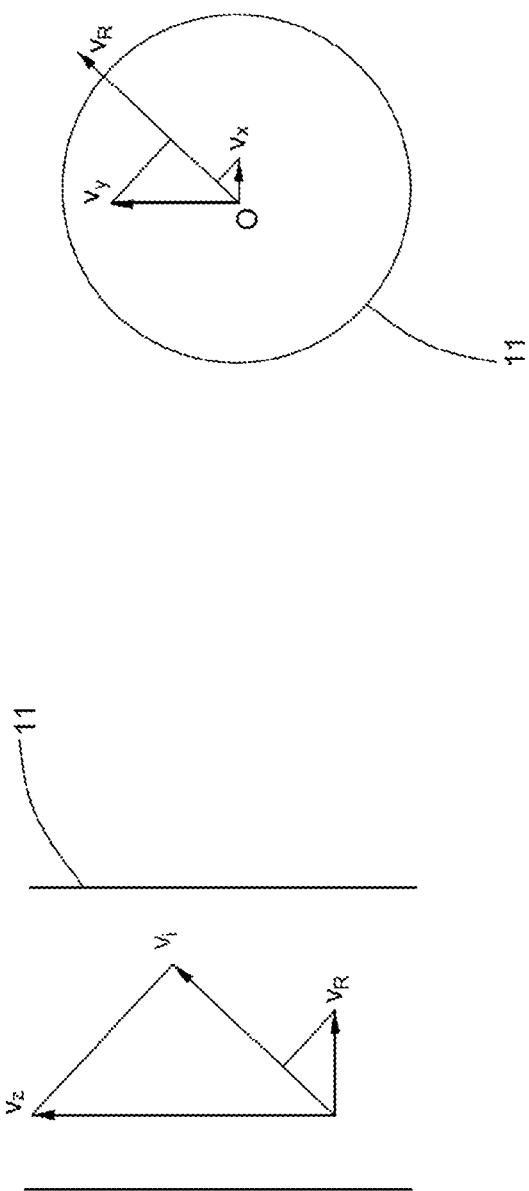
FIG. 1A is the axial schematic drawing of riser pipe.
FIG. 1B is the horizontal schematic drawing of riser pipe.
Figure 2:
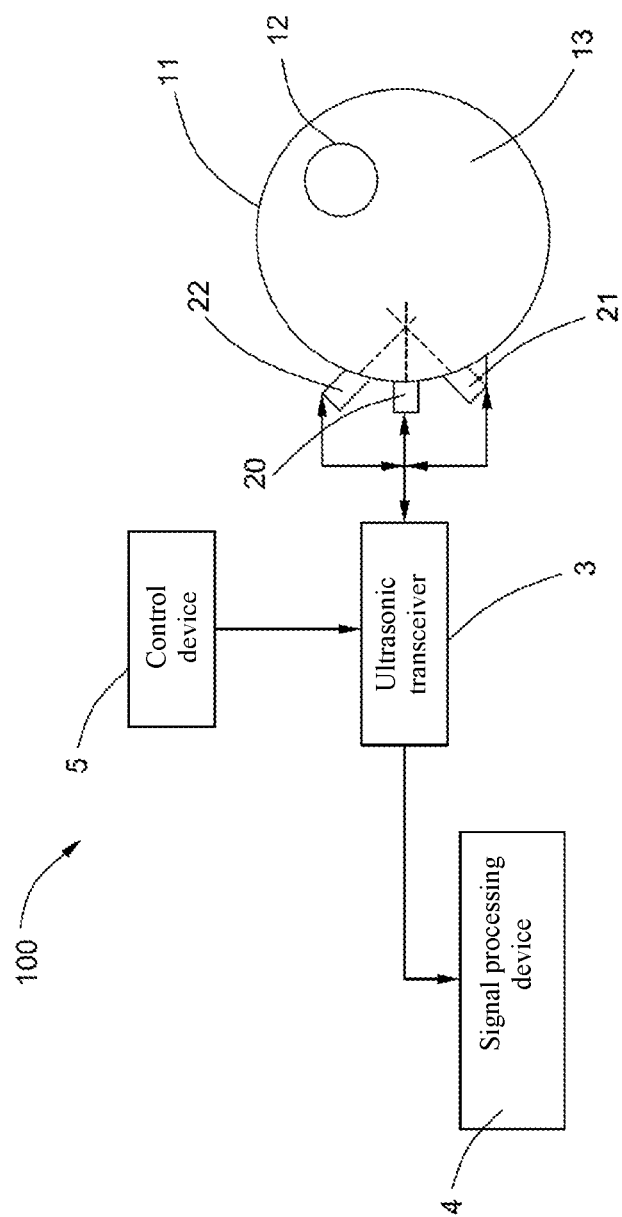
FIG. 2 is the schematic drawing of an embodiment of the system used to calculate the flow rate.
Figure 3:
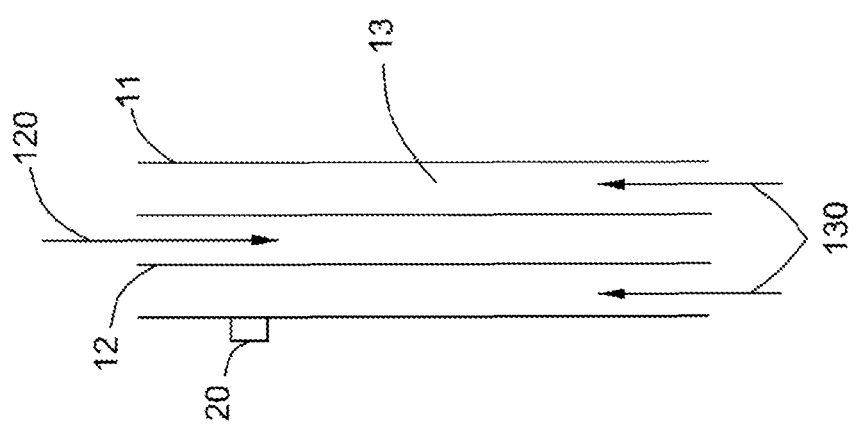
FIG. 3 is the sectional view of riser pipe in drawing 2.
Figure 4:
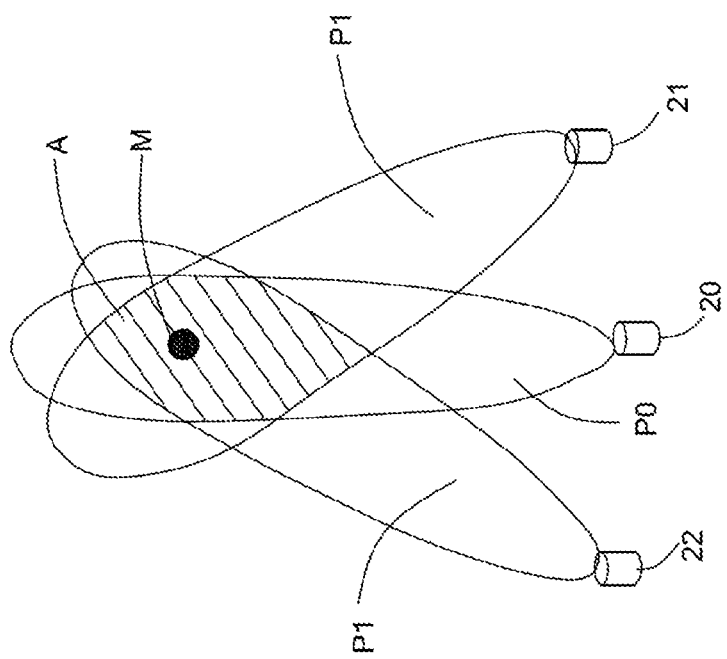
FIG. 4 is the schematic drawing of ultrasonic beam path of three ultrasonic sensors in drawing 2.
Figure 5:
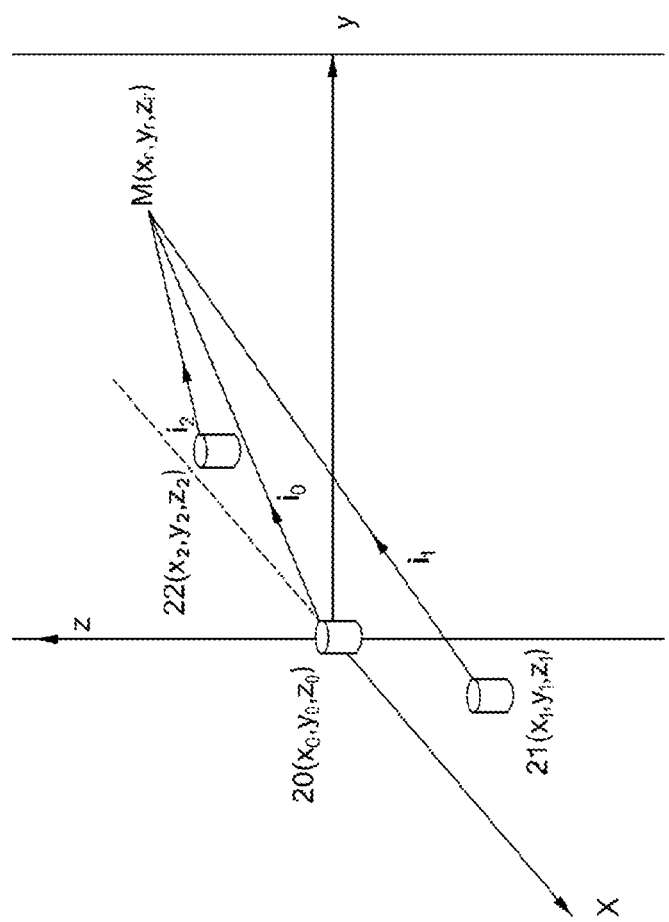
FIG. 5 is the schematic drawing of three-dimensional coordinate system built on three ultrasonic sensors.
Figure 6:
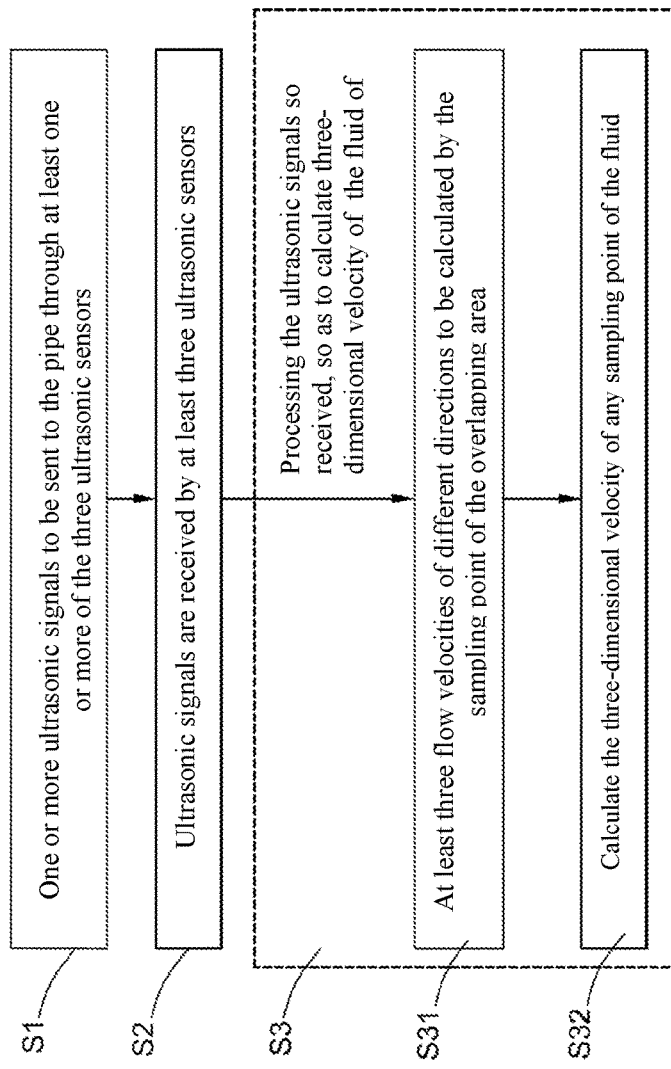
FIG. 6 is the flow chart of an embodiment of the method that is used to calculate the three-dimensional flow rate.

In order to assist the technical personnel of this domain to precisely understand embodiments of the invention, embodiments of this invention will be described below together with attached drawings. In the detailed description, this specification would not describe in detail the known function or structure to avoid the unnecessary details which would influence the disclosure of this invention.

Unless otherwise defined, the technical terms and scientific terms used in this claims and specification shall contain the ordinary meaning that could be understood by the general technical personnel of the technical domain which this invention belongs to. The words like "first", "second" and other similar words used in this specification and claims do not represent any sequence, quantity or importance, but only is used to distinguish the different compositions. The words like "one", "a" or other similar words do not represent the limit of quantity, but only represent that at least one existence. The words like "including", "containing" or other similar words represents that the components or item before the words like "including" or "containing" covering the components or items and its equivalent components listed behind the words like "including" or "containing", and shall not be exclusive of other components or items. The words like "connecting" or "linking" or other similar words is not limited within the physical or mechanical connection, but also could contain the electrical connection, no matter direct or indirect.

The system 100 and method used to calculate flow rate in an embodiment are provided to solve the mentioned technical problem in the current technology. The system 100 and method that used to calculate flow rate are described in detail below.

The schematic drawing of an embodiment of the system 100 and method that used to calculate the flow rate is shown in drawing 2. Hereby, by referring to drawing 2, a specific embodiment for the system 100 and method that used to calculate the flow rate could be applied in drilling the shaft at sea or shaft on ground, which contains pipe 11, at least two ultrasonic sensors (ultrasonic sensors 20, 21 and 22 as shown in the drawing), ultrasonic transmit and receive device 3 that electrically connecting with at least two ultrasonic sensors (like ultrasonic sensors 20, 21 and 22) and signal processing device 4 that electrically connecting with ultrasonic transmit and receive device 3. Within an example, the pipe 11 is shown as riser pipe, further, the pipe 11 would be described with riser pipe as example. However, this would only be an illustrative example of pipe 11, and the pipe 11 would not be limited within the scope of the above-mentioned illustrative example. In an example, the pipe 11 could also be casing pipe. Within an embodiment that not defined, each of at least two ultrasonic sensors (like ultrasonic sensors 20, 21 and 22) are Doppler ultrasonic sensors, with high accuracy of induction. Of cause, the type of ultrasonic sensor is not limited within the above-mentioned, and other proper sensors could also be used.

The sectional view of riser pipe 11 of drawing 2 is shown in drawing 3, further, as shown in drawing 2 together with drawing 3, the riser pipe 11 contains the cylindrical section (as shown in drawing 1B), and could accept drill rod 12, the annular space 13 that used for the drilling fluid 130 flowing through is formed between the riser pipe 11 and drill rod 12, the drill rod 12 is formed by multiple pipes with a certain of length connecting with each other end to end, and the drilling rod 12 is installed in the riser pipe 11 and extends in the riser pipe 11 along with the axis direction of riser pipe 11. The rotatable drill bit could be installed on the bottom of drill bit 12 (not shown in drawing), to drill the shaft by utilizing the riser pipe 11, drill rod 12 and the drill bit thereon. The drilling fluid 120 (not shown in drawing) (usually also be called as drilling mud) is delivered to shaft via the drill rod 12. During the drilling process, the drilling fluid 130 returned from shaft could be returned to the platform via the annular space 13 between the riser pipe 11 and drill rod 12. The drilling fluid 120 maintains a certain level of hydrostatic pressure to balance the pressure of drilling fluid 130 returned from shaft and to cool down the drill bit, further, in the meantime, the drilling fluid 120 carries the material generated during drilling process, like fragmented rock, etc. to the sea surface. Within an embodiment, the drilling fluid 120 from the platform could contain water or oil and multiple additive substances. The drilling fluid 130 returned could at least contain the mixture of drilling fluid 120 and the materials generated during drilling process. On the platform, the drilling fluid 130 returned could be processed like filtered, to remove the solid material therein and to be recycled for usage.

In an embodiment of the method, at least two or three ultrasonic sensors are used. Taking the diagram for an example, at least three ultrasonic sensors 20, 21 and 22 are selected in an embodiment of the method, and 20, 21 and 22 can be the same. In one of the embodiments of the method, no less than three ultrasonic sensors 20, 21, 22 are set up around stand pipe 11, three ultrasonic sensors 20, 21, 22 are installed on the surface of stand pipe 11, however, the set position of three ultrasonic sensors 20, 21, 22 are not limited to those places. In embodiments, at least three ultrasonic sensors 20, 21 and 22 can also be set on the inner surface of or inside of stand pipe 11, which can contact drilling fluid 130 as a non-contact sensor for monitoring. Also, as shown in reference Drawing 4, the settings of three ultrasonic sensors 20, 21 and 22 enable the said three ultrasonic sensors 20, 21 and 22 to have different ultrasonic beam path P0, P1 and P2, and ultrasonic beam path P0, P1 and P2 of three ultrasonic sensors 20, 21, 22 go cross with each other to create overlapping area A, in addition, ultrasonic beam path P0, P1 and P2 of three ultrasonic sensors 20, 21, 22 are located in different surface respectively.

Ultrasonic transceiver 3 is used to activate three ultrasonic sensors 20, 21 and 22 at least, and send one or multiple signals through annular space 13 between one or more stand pipes 11 traversing less than three ultrasonic sensors 20, 21 and 22 with drill pipe 12, in an embodiment of the method, ultrasonic transceiver 3 sends signal to the annular space 13 between stand pipe 11 and drill pipe 12 through one of at least three ultrasonic sensors 20, 20 and 22 (such as ultrasonic sensor 20), and it also receives signal through ultrasonic sensor 20, 21 and 22

Signal processing device 4 receives ultrasonic signals and process them to calculate the returned three-dimensional velocity $\underline{v}(v_x, v_y, v_z)$ of drilling fluid 130.

Drawing 5 shows the schematic diagram of a three-dimensional coordinate system use established by at least three ultrasonic sensors 20, 21 and 22, the three-dimensional coordinate system shown in Drawing 5 is built based on the origin of ultrasonic sensor 20 coordinate system, all origins of other coordinates also take it as a basis. The three-dimensional coordinate systems of ultrasonic sensor 20, 21 and 22 are 20 $(x_0, y_0, z_0)$, 21 $(x_1, y_1, z_1)$ and 22 $(x_2, y_2, z_2)$ respectively; M is a sampling point in overlapping area A, its three-dimensional coordinate is M $(x_r, y_r, z_r)$; $\underline{i}_0$、$\underline{i}_1$、$\underline{i}_2$ are direction variables along the ultrasound beam paths of three ultrasonic sensors 20, 21 and 22 respectively. With the reference to and as shown in Drawing 4 and Drawing 5, we can conclude that signal processing device 4 calculates at least three velocities $\underline{v}_0$、$\underline{v}_1$ and $\underline{v}_2$ of random sampling point M $(x_r, y_r, z_r)$ at different directions in overlapping area A based on the ultrasonic signal received, for example, each of the three velocities $\underline{v}_0$、$\underline{v}_1$、$\underline{v}_2$ at different directions can be calculated by the Doppler signal processing method. In an embodiment, at least three ultrasonic sensors 20, 21 are 22 regarded as the same.

Then, signal processing device 4 computes the three-dimensional velocity $\underline{v}(v_x, v_y, v_z)$ of random sampling point M of returned drilling fluid 130 according to the following formula based on at least three velocities $\underline{v}_0$、$\underline{v}_1$ and $\underline{v}_2$ of random sampling point M $(x_r, y_r, z_r)$ at different directions in overlapping area.

$$f_0 = -\frac{f_c}{c} 2\underline{v}_0 = -\frac{f_c}{c} 2(\underline{v} \cdot i_0) \quad (1)$$

$$f_1 = -\frac{f_c}{c}(\underline{v}_0 + \underline{v}_1) = -\frac{f_c}{c}(\underline{v} \cdot i_0 + \underline{v} \cdot i_1) \quad (2)$$

$$f_2 = -\frac{f_c}{c}(\underline{v}_0 + \underline{v}_2) = -\frac{f_c}{c}(\underline{v} \cdot i_0 + \underline{v} \cdot i_2) \quad (3)$$

$$\underline{v} = (v_x, v_y, v_z) \quad (4)$$

$$i_i = (i_{ix}, i_{iy}, i_{iz}), i = [0, 2] \quad (5)$$

Wherein $f_0$、$f_1$、$f_2$ are the frequency deviations of ultrasonic signals received by three ultrasonic sensors 20, 21 and 22 respectively, $f_c$ is the center frequency of ultrasonic signal launched by ultrasonic sensor 20, c is sound velocity, $\underline{v}$ is the velocity variable of returned drilling fluid 130 (which is three dimensional flow velocity in an embodiment of the method), $i_i$ (i=[0, 2]) is direction variable of any beam path along three ultrasonic sensors 20, 21 and 22 respectively.

Based on formulas (1) to (5), the following formula can be derived:

$$\begin{bmatrix} i_{0x} & i_{0y} & i_{0z} \\ i_{1x}+i_{0x} & i_{1y}+i_{0y} & i_{1z}+i_{0z} \\ i_{2x}+i_{0x} & i_{2y}+i_{0y} & i_{2z}+i_{0z} \end{bmatrix} \begin{bmatrix} v_x \\ v_y \\ v_z \end{bmatrix} = \begin{bmatrix} -\frac{f_0 c}{2f_c} \\ -f_1 \frac{c}{f_c} \\ -f_2 \frac{c}{f_c} \end{bmatrix} \quad (6)$$

$$i_0 = (x_r - x_0, y_r - y_0, z_r - z_0)/r_0 \quad (7)$$

$$r_0 = \sqrt{(x_r - x_0)^2 + (y_r - y_0)^2 + (z_r - z_0)^2} \quad (8)$$

$$i_1 = (x_r - x_1, y_r - y_1, z_r - z_1)/r_1 \quad (9)$$

$$r_1 = \sqrt{(x_r - x_1)^2 + (y_r - y_1)^2 + (z_r - z_1)^2} \quad (10)$$

$$i_2 = (x_r - x_2, y_r - y_2, z_r - z_2)/r_2 \quad (11)$$

$$r_2 = \sqrt{(x_r - x_2)^2 + (y_r - y_2)^2 + (z_r - z_2)^2} \quad (12)$$

According to the above method, all three-dimensional velocities of random sampling points in overlapping area A can be calculated based on the coordinates of random sampling point M $(x_r, y_r, z_r)$ of the overlapping area A.

Coordinate system as shown in Drawing 5 is only demonstrated as an example of the present invention, and can't be regarded as a limitation to the present invention. Actually, based on the above formula, we can find the coordinates used in the calculation of three-dimensional velocity $\underline{v}(v_x, v_y, v_z)$ of random sampling point M of returned drilling fluid 130 are relative coordinate values of three ultrasonic sensors 20 $(x_0, y_0, z_0)$, 21 $(x_1, y_1, z_1)$ and 22 $(x_2, y_2, z_2)$, therefore, the calculation of three-dimensional velocity $\underline{v}(v_x, v_y, v_z)$ of random sampling point M$(x_r, y_r, z_r)$ of the returned drilling fluid 130 is not related to the establishment of a coordinate system and the selection of its origin.

Signal processing device 4 used in embodiments of the present invention is not limited to any processing device. In an embodiment, the signal processing device 4 can be substituted by any compatible device, which can operate or make calculation, as well meeting the other requirements of the embodiment. Technical personnel in the field understand that the signal processing device 4 may receive input and process it according to the scheduled rules, so as to generate the output.

As shown in Drawing 2, system 100 used to calculate flow velocity is comprised of control device 5, and ultrasonic transceiver 3 which is under the restriction of control device 5, it launches ultrasonic signal by ultrasonic sensor 20 and receives ultrasonic signals by ultrasonic sensor 20, 21 and 22.

When ultrasonic transceiver 3 sends one or multiple signals through annular space 13 between stand pipe 11 and the drilling pipe 12 of at least three ultrasonic sensors 20, 21 and 22, or when the ultrasonic sensors 20, 21 and 22 are different sensors, the three-dimensional flow velocity $\underline{v}(v_x, v_y, v_z)$ at random sampling point M of returned drilling fluid 130 can be calculated based on the above-mentioned method, and do not need to be repeated here.

In an embodiment of the method, at least two ultrasonic sensors are needed (e.g., select any two ultrasonic sensors from ultrasonic sensors 20, 21 and 22) in the calculation of two-dimensional velocity $\underline{v}(v_R, v_z)$ of returned drilling fluid 130. In the calculation of three-dimensional velocity $\underline{v}(v_x, v_y, v_z)$ of returned drilling fluid 130, as there are three variables $v_x, v_y, v_z$, so it is needed to solve three equations, while in the calculation of two-dimensional velocity $\underline{v}(v_R, v_z)$ of returned drilling fluid 130, there are only two variables, so just two equations should be solved, therefore, only two ultrasonic sensors are needed. Similarly, the two ultrasonic sensors have different ultrasonic beam paths respectively, and their beam paths intersect with each other. Ultrasonic transceiver 3 sends one or two signals through annular space 13 between one or more stand pipes 11 drill pipe 12, and receives ultrasonic signal through two ultrasonic sensors. Signal processing device 4 receives ultrasonic signal, and the calculation of two-dimensional velocity of returned drilling fluid 130 can take reference by the above-mentioned three-dimensional velocity calculation method, and it will be simplified compared with the calculation of two-dimensional velocity of returned drilling fluid 130, so there will be no further description.

In an embodiment, the system 100 for flow velocity calculation can take at least two of the ultrasonic sensors 20, 21, 22 mentioned above as one group of sensors, and the system 100 may also include at least one group of these sensors. When the system 100 for flow velocity calculation includes multi-groups of these ultrasonic sensors, these multi-groups of these ultrasonic sensors can operate alternatively in the embodiment. For instance, when the ultrasonic beam paths of these sensors form the overlapping area, these multi-groups of ultrasonic sensors can operate alternatively to avoid the signal interference. In an embodiment, the multi-groups of ultrasonic sensors can operate at the same time. And the ultrasonic beam paths of the sensors in different operating groups will not form the overlapping area, which can avoid the signal interference. The multi-groups of ultra-sonic sensors are located in different points of the stand pipe 11, which can record and calculate the flow velocity of the returned drilling fluid 130 at different area of the standpipe 11.

In an embodiment, these multi-groups of ultrasonic sensors can be placed at the circumferential direction of the stand pipe 11, which can calculate the flow velocity of the returned drilling fluid 130 at the different points of the circumferential direction of the stand pipe 11. In an embodiment, these multi-groups of ultrasonic sensors can be set at the axial direction of the stand pipe 11, which can calculate the flow velocity of the returned drilling fluid 130 at the different points of the axial direction of the stand pipe 11.

In the practical application in the drilling field, the system 100 for flow velocity calculation can calculate the flow velocity of the returned drilling fluid 130 precisely even when the drill pipe 12 is moving, namely the two-dimensional flow velocity $\underline{v}(v_R, v_z)$ or the three-dimensional flow velocity $\underline{v}(v_x, v_y, v_z)$. Then it can calculate the flux of the returned drilling fluid 130 more precisely, which can improve the flux measurement preciseness of the returned drilling fluid 130, and help to calculate the position and the moving condition of the drill pipe 12. Embodiments of the present invention may have high application value and reliability within the drilling field.

The application of the system 100 for flow velocity calculation does not limit to the drilling field but include other multiple fields. The system 100 can calculate the flow velocity of any fluid in any pipes, which may show high application value and reliability in the field.

An embodiment also provides a method to calculate the flow velocity with the system 100. Similarly, the other methods for flow velocity calculation can be used to calculate the flow velocity of any fluid in any pipes. The method of flow velocity calculation based on an embodiment includes the following steps.

Place at least two ultrasonic sensors around the pipe, and one or more than one of these sensors can send one or multiple ultrasonic signals to the pipe. Then at least two ultrasonic beam paths of these sensors intersect with each other and form the overlapping area. Among them, for instance, every sensor operates in the Doppler mode.

Then we can receive the ultrasonic signals via at least two ultrasonic sensors.

Process the received ultrasonic signals, and calculate the flow velocity of the fluid in the pipe. For instance, when being applied to the drilling field, the flow velocity calculation method embodiment can calculate the flow velocity of the returned drilling fluid 130 within the annular space 13.

An embodiment of the method can also calculate the two-dimensional or three-dimensional flow velocity of the fluid in the pipe as required by the practical application. When the two-dimensional flow velocity is required in the practical application, one or two of the two ultrasonic sensors (such as any two of the sensors 20, 21 and 22) can emit one or two ultrasonic signals to the pipe, and the ultrasonic beam paths of these two sensors will intersect with each other and form the overlapping area. Then these two ultrasonic sensors will receive and process the signals, and then calculate the two-dimensional flow velocity of the fluid in the pipe.

In the practical application, if it is required to calculate the three-dimensional velocity of fluid, under which circumstances, two ultrasonic sensors shall include at least three ultrasonic sensors, e.g. three ultrasonic sensors 20, 21 and 22. Detailed explanations shall be made by using the following example: how to calculate the three-dimensional velocity of fluid.

Drawing 6 has shown a flow chart for a method that is hereby invented and designed to calculate the three-dimensional velocity based on an embodiment. As shown in Drawing 6, steps as follows are included for a method that is designed to calculate the three-dimensional velocity based on an embodiment.

In the step S1, at least three ultrasonic sensors 20, 21, and 22 shall be arranged to the extent that at least three ultrasonic sensors 20, 21, and 22 have different ultrasonic beam paths P0, P1 and P2. Meanwhile, the ultrasonic-beam paths P0, P1 and P2 of at least three ultrasonic sensors 20, 21 and 22 are intersected with each other and are overlapped in area A. One or more ultrasonic signal(s) shall be transmitted to channels through at least one or more sensors among the three ultrasonic sensors 20, 21 and 22. The ultrasonic-beam paths of at least three ultrasonic sensors are located in varying planes.

In step S2, ultrasonic signals shall be received from at least three ultrasonic sensors 20, 21 and 22.

In step S3, the processing of the received ultrasonic signals shall refer to the method introduced above in which the system 100 is described and the three-dimensional velocity $\underline{v}(v_x, v_y, v_z)$ of fluid can be calculated when the fluid flows in the channels.

As shown in Drawing 6, step S3 further includes the following steps: In step S31, at least three current velocities $\underline{v}_0 、 \underline{v}_1 、 \underline{v}_2$ of three different directions shall be calculated according to the ultrasonic signals so received after random sampling points M $(x_r, y_r, z_r)$ located in the overlapped area A by the Doppler signal-processing algorithms.

In step S32, based on the three current velocities $\underline{v}_0 、 \underline{v}_1 、 \underline{v}_2$ calculated at the different directions where the random sampling points M $(x_r, y_r, z_r)$ are located, three-dimensional velocity $\underline{v}(v_x, v_y, v_z)$ of the random sampling points M $(x_r, y_r, z_r)$ of the fluid shall be calculated. Particularly, based on the three current velocities $\underline{v}_0 、 \underline{v}_1 、 \underline{v}_2$ at least that have been calculated at the different directions where the random sampling points M $(x_r, y_r, z_r)$ are located, at least three ultrasonic sensors 20 (x0, y0, z0), 21 (x1, y1, z1), 22 (x2, y2, z2) and the relative positions between and among the random sampling points M $(x_r, y_r, z_r)$, three-dimensional velocity $\underline{v}(v_x, v_y, v_z)$ of the random sampling points M $(x_r, y_r, z_r)$ of the fluid shall be calculated by the above formulas (6)-(12).

In an embodiment, the methods designed to calculate the current velocity shall also include: by providing at least one group of ultrasonic sensors, wherein, each group of ultrasonic sensors includes at least the above-mentioned ultrasonic sensors. In an embodiment, at least one group of ultrasonic sensors include multiple-groups of ultrasonic sensors, meanwhile, the paths of ultrasonic beams are overlapped in some areas, then the multiple groups of ultrasonic sensors in which overlapped areas exist can be in operation alternatively. In an embodiment, when at least one group of ultrasonic sensors include multiple sub-groups of ultrasonic sensors, meanwhile, the ultrasonic-beam paths of such multiple sub-groups of ultrasonic sensors have no overlapped areas, and then the multiple sub-groups of ultrasonic sensors without possessing overlapped areas shall be operated simultaneously.

In an embodiment, the method designed to calculate the current velocity can be applied into many areas and is of relatively high application value and reliability in the field. When it is applied to the practical drilling field, even under the circumstances that drill pipe 12 moves, it shall also be possible to accurately calculate out the current velocity of returned drilling fluid 130, i.e., two-dimensional current velocity or three-dimensional current velocity and further to be able to calculate out the flow rate of the returned drilling fluid 130 more accurately, enhance the accuracy of the measurement of current velocity of recurrent drilling fluid 130 as well as contributing to calculate out the position and status of movement of drilling pipe 12, it is of relatively high application value and reliability in drilling field.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for calculating a velocity of a fluid flow passing through a conduit, the system comprising:
   at least two ultrasonic transducers configured to be disposed on the conduit, each of the at least two ultrasonic transducers having a respective beam paths, wherein the at least two ultrasonic transducers are spaced and oriented such that the respective beam paths intersect to provide an overlapped area disposed within the conduit;
   an ultrasonic transceiver configured to energize at least one of the at least two ultrasonic transducers to transmit at least one ultrasonic signal to the conduit through at least one ultrasonic transducers and receive reflected ultrasonic signals from a sampling point within the overlapped area through the at least two ultrasonic transducers, wherein the sampling point is spaced from the conduit; and
   a signal processor for processing the received reflected ultrasonic signals to calculate the velocity of the fluid flow passing through the conduit at the sampling point.

2. The system of claim 1, wherein the at least two ultrasonic transducers comprise three or more ultrasonic transducers and the signal processor processes the received ultrasonic signals of each of the three or more ultrasonic transducers to calculate a three-dimensional flow velocity of the fluid.

3. The system of claim 2, wherein beam paths of the at least three ultrasonic transducers are located in different planes.

4. The system of claim 1, wherein each of the at least two ultrasonic transducers is a Doppler ultrasonic transducer.

5. The system of claim 1, wherein the at least two ultrasonic transducers are identical.

6. The system of claim 1, wherein the at least two ultrasonic transducers comprise at least one group of ultrasonic transducers.

7. The system of claim 6, wherein the at least one group of ultrasonic transducers comprises a plurality of groups of ultrasonic transducers wherein the plurality of groups of ultrasonic transducers are disposed on different positions of the conduit for calculating velocities of the fluid flow in different regions within the conduit at different sampling points.

8. A method for calculating a velocity of a fluid flow passing through a conduit, the method comprising:
   orienting at least two ultrasonic transducers in spaced relation and coupled to the conduit such that respective beam paths of the at least two ultrasonic transducers overlap to provide an overlapped area, the overlap area disposed within the conduit;
   transmitting at least one ultrasonic signals through at least one ultrasonic transducer to the conduit;
   receiving reflected ultrasonic signals from a sampling point within the overlapped area through the at least two ultrasonic transducers, wherein the sampling point is spaced from the conduit; and
   processing the received reflected ultrasonic signals to calculate the velocity of the fluid flow passing through the conduit at the sampling point.

9. The method of claim 8, further comprising:
   each of the at least two ultrasonic transducers working in a Doppler mode.

10. The method of claim 8, wherein the at least two ultrasonic transducers comprising three or more ultrasonic transducers, the method further comprising:
    transmitting one or more ultrasonic signals through one or more of the at least three ultrasonic transducers;
    receiving reflected ultrasonic signals through the at least three ultrasonic transducers; and
    processing the received reflected ultrasonic signals to calculate a three-dimensional flow velocity of the fluid.

11. The method of claim 10, wherein the method further comprises:
    locating beam paths of the at least three ultrasonic transducers in different planes.

12. The method of claim 10, wherein the processing the received ultrasonic signals to calculate a three-dimensional flow velocity of the fluid further comprises:
    calculating at least three velocities of the fluid flow in different directions within the overlapped area based on the received reflected ultrasonic signals; and
    calculating the three-dimensional flow velocity of the fluid based on the calculated at least three flow velocities of the fluid flow in the different directions.

13. The method of claim 12, wherein the calculating at least three velocities of the fluid flow in different directions within the overlapped area based on the received reflected ultrasonic signals comprises calculating at least three flow velocities in different directions for any sample point within the overlapped area based on the received ultrasonic signals, and the calculating the three-dimensional flow velocity of the fluid flow based on the calculated at least three flow velocities of the fluid flow in the different directions comprises calculating a three-dimensional flow velocity for the any sample point of the fluid flow based on the calculated at least three flow velocities in the different directions for the any sample point and relative positions between the at least three ultrasonic transducers and the any sample point.

14. The method of claim 12, wherein each of the at least three flow velocities of the fluid flow in different directions is calculated based on a Doppler signal processing of the received reflected ultrasonic signals.

15. The method of claim 8, wherein the at least two ultrasonic transducers comprise at least one group of ultrasonic transducers.

16. The method of claim 15, wherein the at least one group of ultrasonic transducers comprises a plurality of groups of ultrasonic transducers, working iteratively.

17. The method of claim 15, wherein the at least one group of ultrasonic transducers comprises a plurality of groups of ultrasonic transducers and the beam paths among the plurality of groups of ultrasonic transducers have no overlapped area while working at the same time.

18. The method of claim 8, wherein the conduit is a riser of a drilling system with a drill rod extending through the riser, and the sampling point is disposed in the fluid flow passing between riser and the drill rod.

19. A measurement system for calculating a three-dimensional velocity of a fluid flow passing through a riser of a drilling system having a drill rod extending through the riser; the measurement system comprising:

at least three ultrasonic transducers configured to be disposed on the riser, each of the at least three ultrasonic transducers having a respective beam paths, wherein the at least three ultrasonic transducers are spaced and oriented such that the respective beam paths intersect to provide an overlapped area disposed within the riser between the riser and the drill rod;

an ultrasonic transceiver configured to energize at least one of the at least three ultrasonic transducers to transmit at least one ultrasonic signal to the riser through at least three ultrasonic transducers and receive reflected ultrasonic signals from a sampling point within the overlapped area through the at least three ultrasonic transducers, wherein the sampling point is spaced from the riser and drill rod; and a signal processor for processing the received reflected ultrasonic signals to calculate the three-dimensional velocity of the fluid flow passing through the riser at the sampling point.

20. A method for calculating a three-dimensional velocity of a fluid flow passing through a riser of a drilling system having a drill rod extending through the riser; the method comprising:

orienting at least three ultrasonic transducers in spaced relation and coupled to the conduit such that respective beam paths of the at least three ultrasonic transducers overlap to provide an overlapped area, the overlap area disposed within the riser between the riser and the drill rod;

transmitting at least one ultrasonic signal through at least one of the at least three ultrasonic transducers to the riser;

receiving reflected ultrasonic signals from a sampling point within the overlapped area through the at least three ultrasonic transducers, wherein the sampling point is spaced from the riser and drill rod; and processing the received reflected ultrasonic signals to calculate the three-dimensional velocity of the fluid flow passing through the riser at the sampling point.

* * * * *